United States Patent
Oyamada

(10) Patent No.: US 12,405,981 B2
(45) Date of Patent: Sep. 2, 2025

(54) INFORMATION PROCESSING APPARATUS, INFORMATION PROCESSING METHOD, AND STORAGE MEDIUM

(71) Applicant: NEC Corporation, Tokyo (JP)

(72) Inventor: Masafumi Oyamada, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 18/554,311

(22) PCT Filed: May 12, 2023

(86) PCT No.: PCT/JP2023/017858
§ 371 (c)(1),
(2) Date: Oct. 6, 2023

(87) PCT Pub. No.: WO2024/236619
PCT Pub. Date: Nov. 21, 2024

(65) Prior Publication Data
US 2025/0086209 A1    Mar. 13, 2025

(51) Int. Cl.
*G06F 16/338*    (2019.01)
*G06F 16/3332*   (2025.01)
*G06F 40/30*     (2020.01)

(52) U.S. Cl.
CPC ........ *G06F 16/3338* (2019.01); *G06F 16/338* (2019.01); *G06F 40/30* (2020.01)

(58) Field of Classification Search
CPC ..... G06F 16/3338; G06F 16/338; G06F 40/30
See application file for complete search history.

(56) References Cited

U.S. PATENT DOCUMENTS

| | | | |
|---|---|---|---|
| 6,804,414 B1 * | 10/2004 | Sakai | H04N 1/00681 |
| | | | 382/296 |
| 6,836,886 B2 * | 12/2004 | Tuerke | H04L 67/02 |
| | | | 707/E17.107 |
| 2005/0138000 A1 * | 6/2005 | Roux | G06F 16/3347 |

(Continued)

FOREIGN PATENT DOCUMENTS

| JP | H07-225772 A | 8/1995 |
|---|---|---|
| JP | 2002-132811 A | 5/2002 |

(Continued)

OTHER PUBLICATIONS

English translation of International Search Report for PCT Application No. PCT/JP2023/017858, mailed on Jul. 25, 2023.

(Continued)

*Primary Examiner* — Etienne P Leroux
(74) *Attorney, Agent, or Firm* — Sughrue Mion, PLLC

(57) ABSTRACT

To improve reliability of a result of language processing carried out with use of a machine learning model, an information processing apparatus includes at least one processor that carries out: an acquisition process of acquiring a target text; an extraction process of extracting a document related to the target text; a rewriting process of rewriting the target text with use of the document; a generation process of generating a text corresponding to the rewritten target text with use of a machine learning model trained to generate a text based on an input text; and an output process of outputting a result obtained by adding information identifying the document to the generated text.

4 Claims, 11 Drawing Sheets

(56) References Cited

U.S. PATENT DOCUMENTS

| | | | |
|---|---|---|---|
| 2012/0078062 A1 | 3/2012 | Bagchi et al. | |
| 2016/0048587 A1* | 2/2016 | Scholtes | G06N 20/00 706/11 |
| 2017/0249314 A1* | 8/2017 | Sakai | G06F 16/24522 |
| 2018/0137434 A1* | 5/2018 | Chen | G06N 20/00 |
| 2020/0279189 A1* | 9/2020 | Yamaguchi | G06F 16/90344 |
| 2023/0353513 A1* | 11/2023 | Sharp | G06N 20/00 |

FOREIGN PATENT DOCUMENTS

| | | |
|---|---|---|
| JP | 2002-207726 A | 7/2002 |
| JP | 2015-087796 A | 5/2015 |
| JP | 2019-049964 A | 3/2019 |
| JP | 2021-086580 A | 6/2021 |
| JP | 2021-111411 A | 8/2021 |
| JP | 3241834 B | 5/2023 |

OTHER PUBLICATIONS

International Search Report for PCT Application No. PCT/JP2023/017858, mailed on Jul. 25, 2023.
Tsukuboshi, "I Used Chrome Extension "WebChatGPT" That Can Overcome Lies of ChatGPT", Developers IO [online], Mar. 26, 2023, pp. 1-5, <URL: https://web.archive.org/web/20230326082709/https://dev.classmethod.jp/articles/web-chatgpt-extension/>.

* cited by examiner

FIG. 7

| Title | Author(s) | Year of Publication | Summary of Paper |
|---|---|---|---|
| Study on Therapeutic Effects of Novel Anti-Cancer Agents | Taro YAMADA, Jiro SUZUKI | 2023 | This study assesses therapeutic effects of novel anti-cancer agents and clarifies effective doses and risks of side effects. |
| Effects of Dietetic Therapy for Hypertensive Patients | Hanako SATO, Ichiro TANAKA | 2022 | The authors investigated effects of dietetic therapy for hypertensive patients, and proposes diets which contributes to lowering of blood pressure and improvement of quality of life. |
| Evaluation of Effects of Kinesitherapy in Diabetic Patients | Shinichi ITO, Miho KOBAYASHI | 2023 | This study evaluates effects of kinesitherapy in diabetic patients to identify the optimal intensity and duration of exercise. |
| Development of Novel Drug for Dementia Treatment | Kenta WATANABE, Ryoko NAKAMURA | 2021 | In this study, the authors developed a novel drug for the treatment of dementia, which shows hopeful results in experimental models. |
| Study on Effects of Music Therapy on Autistic Children | Naoto TAKAHASHI, Eri HAYASHIDA | 2023 | This study evaluates the possibility of contributing to improvement in communication ability by examining effects of music therapy on autistic children. |

FIG. 8

| Name of Doctor | Workplace | Career (graduation year) | Specialty | ... |
|---|---|---|---|---|
| Taro YAMADA | Tokyo Central Hospital | Tokyo Chuo University (2005) | Cardiovascular surgery | |
| Jiro SUZUKI | Osaka Municipal General Medical Hospital | Nishi Osaka University, Faculty of Medicine (2008) | Oncology | |
| Hanako SATO | Nagoya Kita University Hospital | Nagoya Kita University, Faculty of Medicine (2010) | Pediatrics | |
| Ichiro TANAKA | Fukuoka Prefectural Fukuoka Minami Hospital | Fukuoka Minami University, Faculty of Medicine (2007) | Orthopedic surgery | |
| Shinichi ITO | Sapporo Municipal Sapporo Higashi Hospital | Hokkaido Medical University, Faculty of Medicine (2006) | Neurology | |
| Miho KOBAYASHI | Hiroshima Prefectural Hiroshima Medical Center | Chugoku University, Faculty of Medicine (2011) | Dermatology | |
| Kenta WATANABE | Sendai Municipal General Hospital | Sendai Medical University, Faculty of Medicine (2009) | Ophthalmology | |

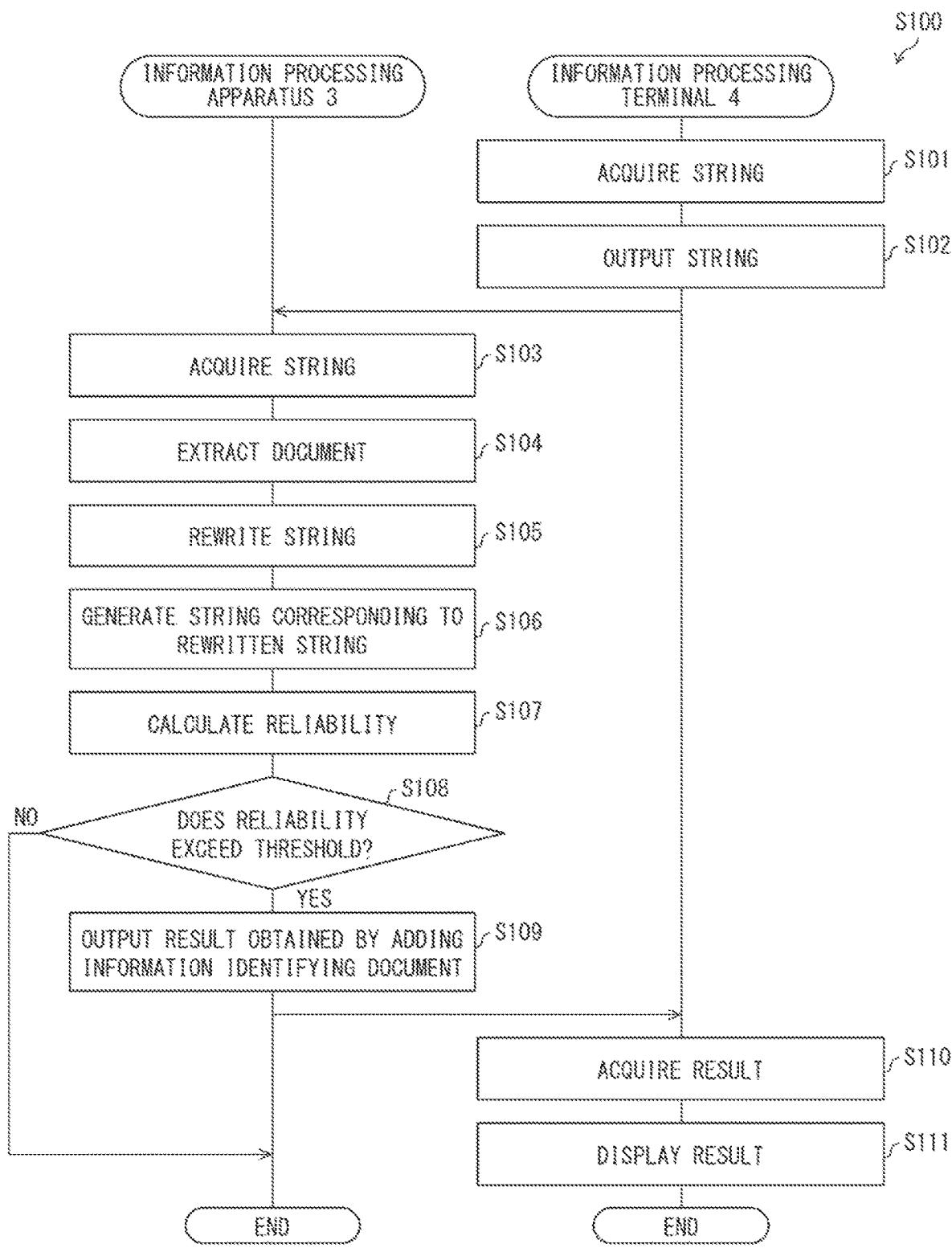

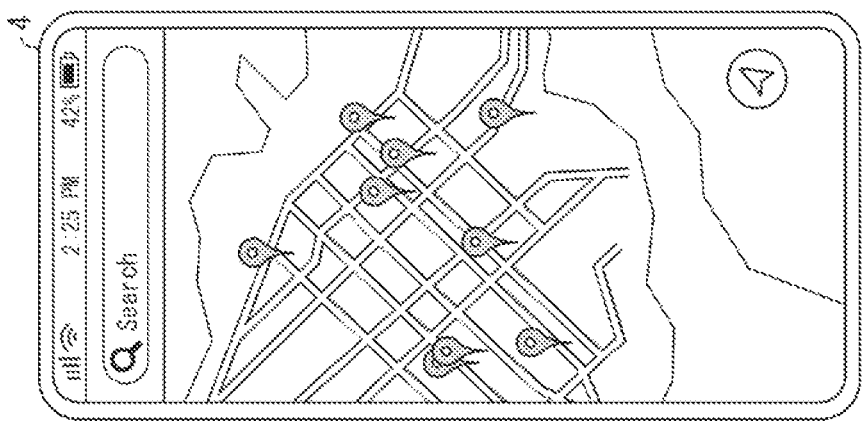
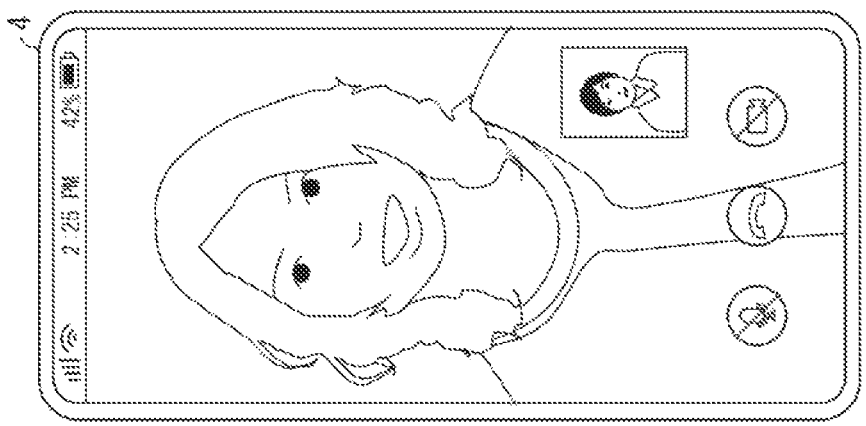
FIG. 10
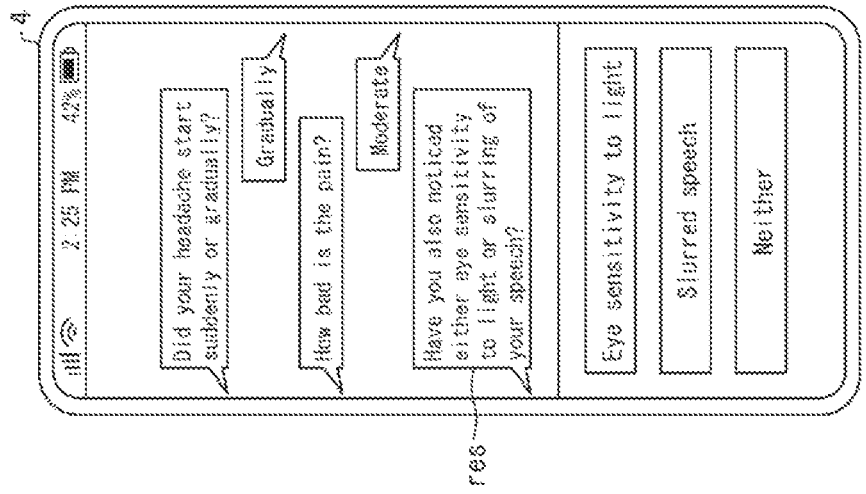

INFORMATION PROCESSING APPARATUS, INFORMATION PROCESSING METHOD, AND STORAGE MEDIUM

This application is a National Stage Entry of PCT/JP2023/017858 filed on May 12, 2023, the contents of all of which are incorporated herein by reference, in their entirety.

TECHNICAL FIELD

The present invention relates to an information processing apparatus, an information processing method, and a storage medium, all of which carry out language processing on text.

BACKGROUND ART

Techniques that use language models are known. The language models are trained by using text data and are configured to carry out language processing.

Patent Literature 1 discloses a question response apparatus that generates a response to a question sentence based on entities extracted from the question sentence and a value of the perplexity of a language model calculated from the question sentence, the model assuming question sentences of a specific field.

The question response apparatus divides the text of the question sentence into morphemes, which are the smallest units having meanings, that is, words. Then, the apparatus issues a request for keyword search to an external search engine by using nouns included in the words as keywords. Further, the question response apparatus uses a response from the external search engine as the answer to the input question sentence.

CITATION LIST

Patent Literature

Patent Literature 1

Japanese Patent Application Publication Tokukai No. 2015-87796

SUMMARY OF INVENTION

Technical Problem

The question response apparatus disclosed in Patent Literature 1 has not verified whether the response from the external search engine is correct. Therefore, there might be a problem in that the response to the question sentence created by the question answering apparatus is wrong.

An example aspect of the present invention has been made in view of the above problem, and an example object thereof is to provide a technique for improving the reliability of a result of language processing carried out with use of a language model.

Solution to Problem

An information processing apparatus in accordance with an example aspect of the present invention includes at least one processor, the at least one processor carrying out: an acquisition process of acquiring a target text; an extraction process of extracting a document related to the target text; a rewriting process of rewriting the target text with use of the document; a generation process of generating a text corresponding to the rewritten target text with use of a machine learning model trained to generate a text based on an input text; and an output process of outputting a result obtained by adding information identifying the document to the text generated in the generation process.

An information processing method in accordance with an example aspect of the present invention includes: acquiring, by at least one processor, a target text; extracting, by the at least one processor, a document related to the target text; rewriting, by the at least one processor, the target text with use of the document; generating, by the at least one processor, a text corresponding to the rewritten target text with use of a machine learning model trained to generate a text based on an input text; and outputting, by the at least one processor, a result obtained by adding information identifying the document to the text generated in the generating.

A non-transitory storage medium in accordance with an example aspect of the present invention stores a program for causing a computer to carry out: an acquisition process of acquiring a target text; an extraction process of extracting a document related to the target text; a rewriting process of rewriting the target text with use of the document; a generation process of generating a text corresponding to the rewritten target text with use of a machine learning model trained to generate a text based on an input text; and an output process of outputting a result obtained by adding information identifying the document to the text generated in the generation process.

Advantageous Effects of Invention

According to an example aspect of the present invention, it is possible to improve the reliability of a result of language processing carried out with use of a language model.

BRIEF DESCRIPTION OF DRAWINGS

FIG. 7 is a table showing an example of documents in the third example embodiment of the present invention.

FIG. 8 is a table showing an example of information on authors of the documents in the third example embodiment of the present invention.

FIG. 9 is a flowchart illustrating the flow of an information processing method in accordance with the third example embodiment of the present invention.

FIG. 10 is a diagram illustrating an example of images displayed on an information processing terminal in accordance with the third example embodiment of the present invention.

EXAMPLE EMBODIMENTS

First Example Embodiment

The following description will discuss a first example embodiment of the present invention in detail with reference to the drawings. The present example embodiment is a basic form of example embodiments described later.
(Configuration of Information Processing Apparatus 1)

Figure 1:
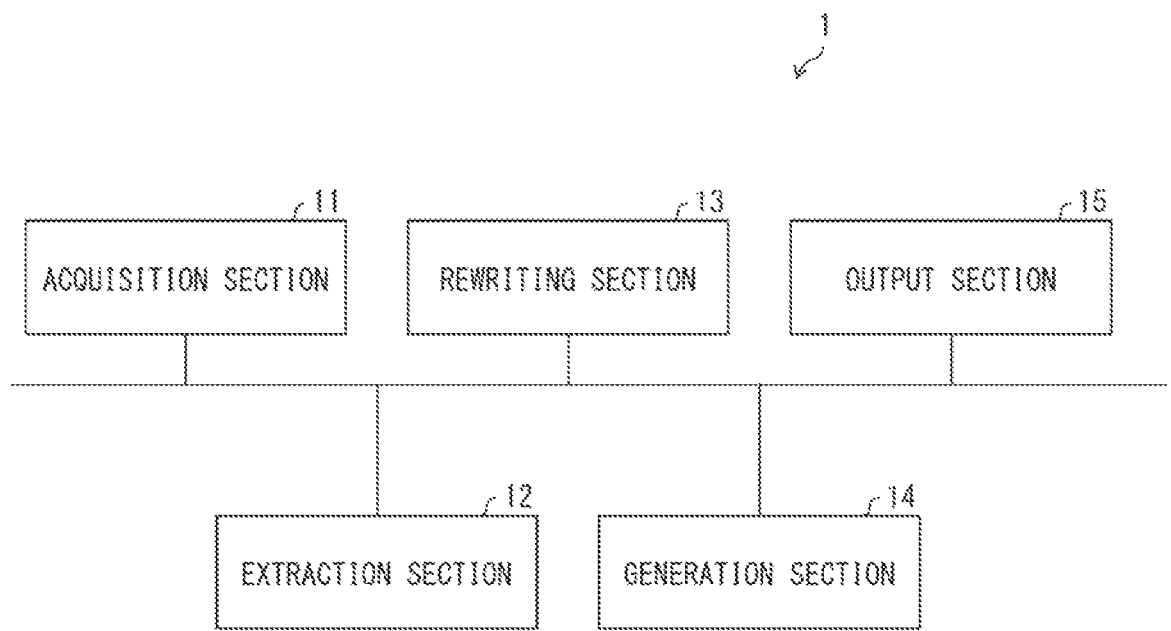
FIG. 1 is a block diagram illustrating the configuration of an information processing apparatus in accordance with a first example embodiment of the present invention.

The following description will discuss the configuration of an information processing apparatus 1 in accordance with the present example embodiment with reference to FIG. 1. FIG. 1 is a block diagram illustrating the configuration of the information processing apparatus 1 in accordance with the present example embodiment.

As illustrated in FIG. 1, the information processing apparatus 1 includes an acquisition section 11, an extraction section 12, a rewriting section 13, a generation section 14, and an output section 15. The acquisition section 11, the extraction section 12, the rewriting section 13, the generation section 14, and the output section 15 are configured to realize acquisition means, extraction means, rewriting means, generation means, and output means, respectively, in the present example embodiment.

The acquisition section 11 acquires a target text. The acquisition section 11 provides the acquired target text to the extraction section 12 and the rewriting section 13.

The extraction section 12 extracts a document related to the target text provided by the acquisition section 11. the extraction section 12 provides the extracted document to the rewriting section 13.

The rewriting section 13 rewrites the target text acquired by the acquisition section 11 with use of the document provided by the extraction section 12. The rewriting section 13 provides the rewritten target text to the generation section 14.

The generation section 14 generates a text corresponding to the target text rewritten by the rewriting section 13, with use of a language model trained to generate a text based on an input text. The generation section 14 provides the generated text to the output section 15.

The output section 15 outputs a result obtained by adding information identifying the document to the text generated by the generation section 14.

As described in the foregoing, the information processing apparatus 1 in accordance with the present example embodiment employs a configuration including: the acquisition section 11 that acquires a target text; the extraction section 12 that extracts a document related to the target text provided by the acquisition section 11; the rewriting section 13 that rewrites the target text acquired by the acquisition section 11 with use of the document provided by the extraction section 12; the generation section 14 that generates a text corresponding to the target text rewritten by the rewriting section 13, with use of a language model trained to generate a text based on an input text; and the output section 15 that outputs a result obtained by adding information identifying the document to the text generated by the generation section 14. Therefore, with the information processing apparatus 1 in accordance with the present example embodiment, it is possible to achieve an example advantage of improving the reliability of the result of the language processing carried out with use of the language model.
(Flow of Information Processing Method S1)

Figure 2:
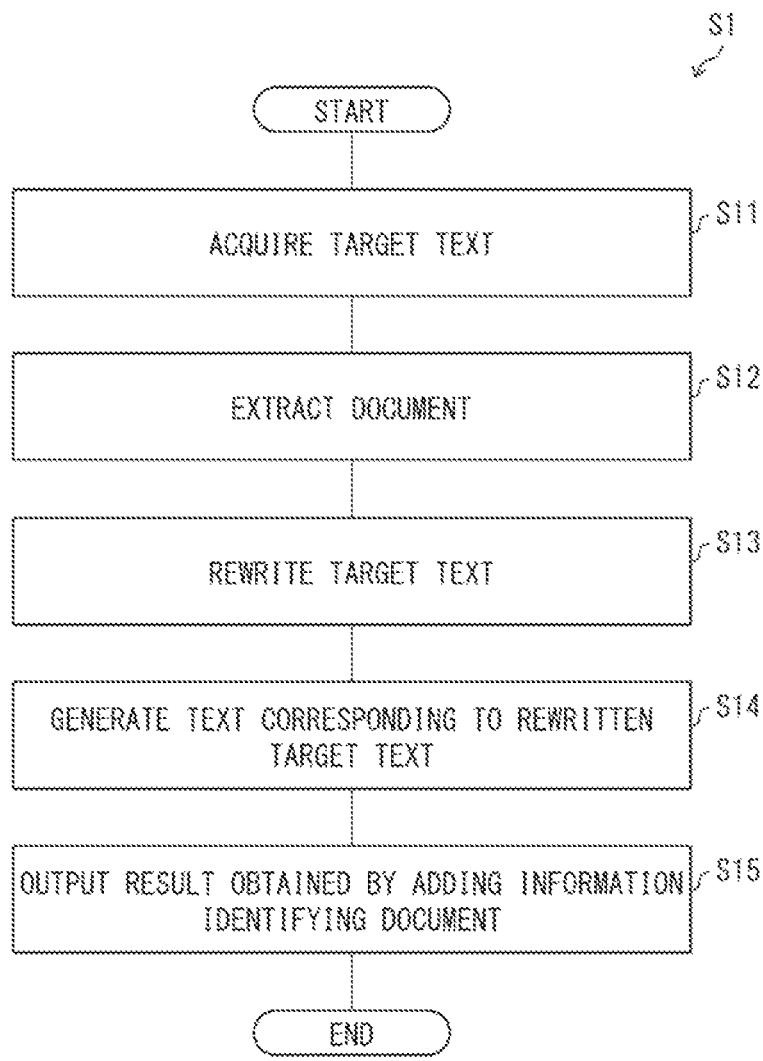
FIG. 2 is a flowchart illustrating the flow of an information processing method in accordance with the first example embodiment of the present invention.

The following description will discuss the flow of an information processing method S1 in accordance with the present example embodiment with reference to FIG. 2. FIG. 2 is a flowchart illustrating the flow of the information processing method S1 in accordance with the present example embodiment.
(Step S11)

In step S11, a target text is acquired. The acquisition section 11 provides the acquired target text to the extraction section 12 and the rewriting section 13.
(Step S12)

In step S12, the extraction section 12 extracts a document related to the target text provided by the acquisition section 11. The extraction section 12 supplies the extracted document to the rewriting section 13.
(Step S13)

In step S13, the rewriting section 13 rewrites the target text acquired by the acquisition section 11 with use of the document provided by the extraction section 12. The rewriting section 13 provides the rewritten target text to the generation section 14.
(Step S14)

In step S14, the generation section 14 generates a text corresponding to the target text rewritten by the rewriting section 13, with use of a language model trained to generate a text based on an input text. The generation section 14 provides the generated text to the output section 15.
(Step S15)

In step S15, the output section 15 outputs a result obtained by adding information identifying the document to the text generated by the generation section 14.

As described in the foregoing, the information processing method S1 in accordance with the present example embodiment employs a configuration including: acquiring, by the acquisition section 11, a target text; extracting, by the extraction section 12, a document related to the target text provided by the acquisition section 11; rewriting, by the rewriting section 13, the target text acquired by the acquisition section 11 with use of the document provided by the extraction section 12; generating, by the generation section 14, a text corresponding to the target text rewritten by the rewriting section 13, with use of a language model trained to generate a text based on an input text; and outputting, by the output section 15, a result obtained by adding information identifying the document to the text generated by the generation section 14. Thus, with the information processing method S1 in accordance with the present example embodiment, an example advantage similar to that of the above-mentioned information processing apparatus 1 is brought about.

Second Example Embodiment

The following description will discuss a second example embodiment of the present invention in detail with reference to the drawings. The same reference numerals are given to constituent elements which have functions identical to those described in the first example embodiment, and descriptions as to such constituent elements are omitted as appropriate.
(Outline of Information Processing Apparatus 2)

An information processing apparatus 2 in accordance with the present example embodiment is an apparatus that acquires a target text and outputs a result obtained by carrying out language processing on the target text. Further, to the result outputted from the information processing apparatus 2, information identifying a document related to the acquired target text is added. The document will be described later. In the following description, the "target text" and the "text" are also referred to as the "string".

The information processing apparatus 2 carries out language processing with use of a language model M trained by using text data. The language model M receives, as input, a string (text) and outputs a result (text) obtained by carrying out language processing on the input string. The result outputted from the language model M may be a string or alternatively, may be an image. The language processing carried out by the language model M is not particularly limited. Examples of the language model M include: a process of generating a text based on an input text; text classification; emotion analysis; information extraction; text summarization; text generation; image generation; and question answering.

The following description will discuss the language model M in detail. The language model M is created by means of learning of the relationship between words in a text (text data), and is a model that generates, from the target string, a related string related to the target string. With use of the language model that has been made to learn statements and texts of various contexts, it is possible to generate the related string of reasonable contents related to the target string.

Examples of the language model M may include, but not limited to: large language models (LLMs) such as Bidirectional Encoder Representations from Transformers (BERT), Generative Pre-trained Transformer (GPT), Text-to-Text Transfer Transformer (T5), Robustly optimized BERT approach (RoBERTa), Efficiently Learning an Encoder that Classifies Token Replacements Accurately (ELECTRA); and learning models created by transfer learning or fine tuning with use of a pre-trained model (e.g., Chat Generative Pre-trained Transformer, ChatGPT).

Further, the string generated by the language model M is not limited to a natural language. The language model M may output an artificial language (program source codes or the like) for, for example, a string inputted in a natural language. For example, the language model M receives, as the target string, input of a question "how to acquire data including a specific string from the database?". For the input, the language model M may output a program source code for carrying out database processing. Alternatively, the language model M may output a natural language corresponding to the string inputted in an artificial language.

The string acquired by the information processing apparatus 2 is not particularly limited, and may be, for example, a string including at least one word and an instruction indicating which language processing is to be carried out. For example, it is assumed that the information processing apparatus 2 acquires a string "what is the main business field of XX Corporation?". In this case, the string includes: five words, that is, "what is", "the main", "business field", "of", and "XX Corporation"; and an instruction to respond to the question stating "what is the main business field of XX Corporation?".

(Configuration of Information Processing Apparatus 2)

Figure 3:
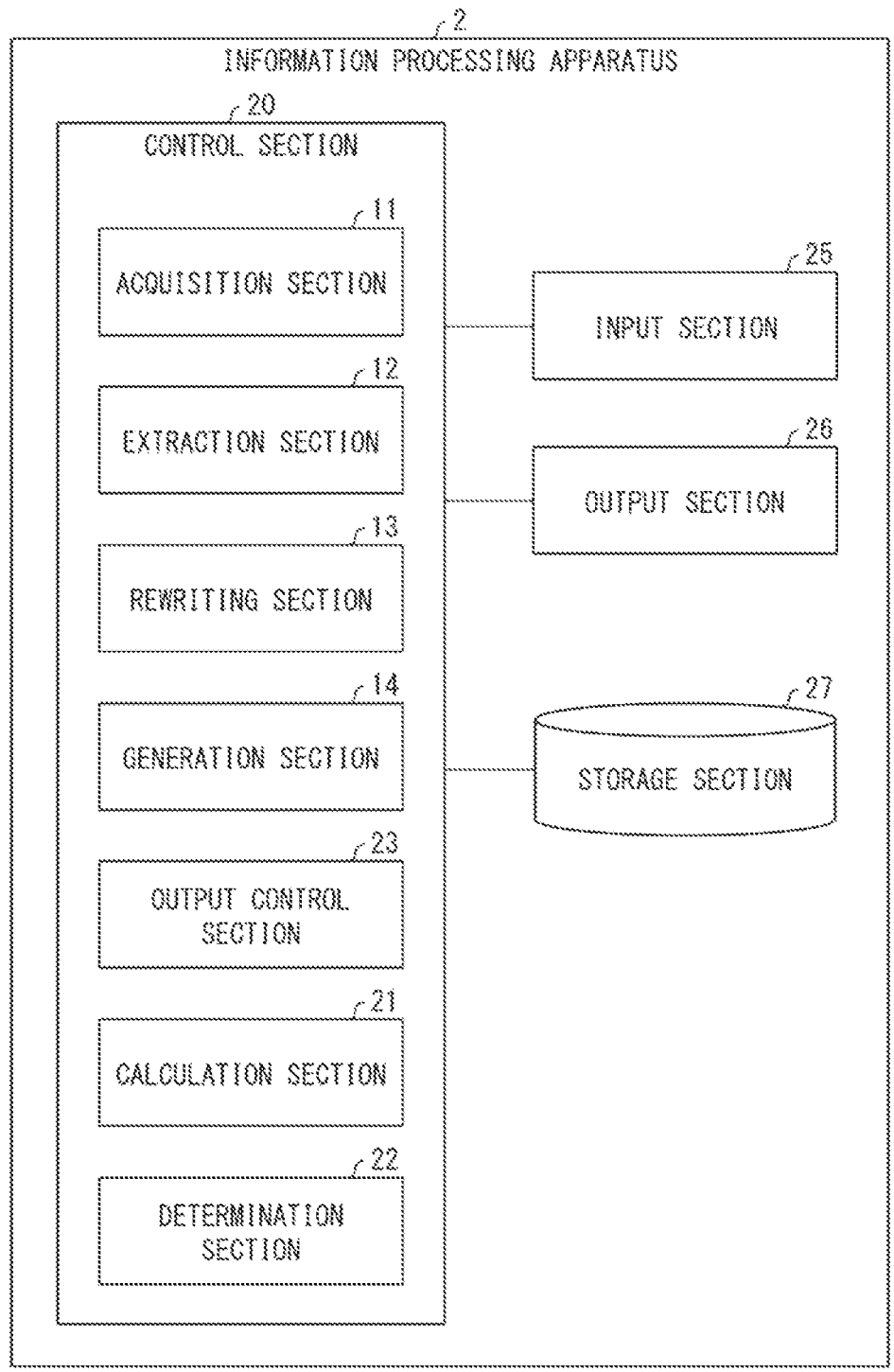
FIG. 3 is a block diagram illustrating the configuration of an information processing apparatus in accordance with a second example embodiment of the present invention.

The following description will discuss the configuration of the information processing apparatus 2 with reference to FIG. 3. FIG. 3 is a block diagram illustrating the configuration of the information processing apparatus 2 in accordance with the present example embodiment.

As illustrated in FIG. 3, the information processing apparatus 2 includes a control section 20, an input section 25, an output section 26, and a storage section 27.

The input section 25 is an interface for receiving input from a user. As an example, the input section 25 provides information indicating the received user input to the control section 20. Examples of the input section 25 may include, but not limited to, a mouse, a keyboard, a touch pad, and a microphone.

The output section 26 outputs data. As an example, the output section 26 may be an interface for outputting data to another apparatus connected thereto. As an example of this case, the output section 26 outputs a result outputted from the control section 20 to the another apparatus connected. As another example, the output section 26 may be a display device that displays an image or may be a speaker that outputs sound. When the output section 26 is the display device, the output section 26 displays an image including the result outputted from the control section 20.

The storage section 27 stores data referred to by the control section 20. An example of the data stored in the storage section 27 may be documents. Examples of the storage section 27 may include, but not limited to, a flash memory, a hard disk drive (HDD), a solid state drive (SSD), and a combination thereof.

The storage section 27 also stores the language model M. It should be noted that "the storage section 27 stores the language model M" means that the storage section 27 stores parameters defining the language model M. The language model may be stored in another storage device (e.g., an external server) other than the storage section 27.

The control section 20 controls constituent elements included in the information processing apparatus 2. Further, as illustrated in FIG. 3, the control section 20 includes an acquisition section 11, an extraction section 12, a rewriting section 13, a generation section 14, an output control section 23, a calculation section 21, and a determination section 22. The acquisition section 11, the extraction section 12, the rewriting section 13, the generation section 14, the output control section 23, the calculation section 21, and the determination section 22 are configured to realize acquisition means, extraction means, rewriting means, generation means, output means, calculation means, and determination means, respectively, in the present example embodiment.

The acquisition section 11 acquires data provided by the input section 25. As an example, the acquisition section 11 acquires a string. In the following description, the string acquired by the acquisition section 11 is also referred to as the first string. The acquisition section 11 stores the acquired first string in the storage section 27.

The extraction section 12 extracts a document related to the string. As an example, the extraction section 12 may extract a document related to the first string from the documents stored in the storage section 27. As another example, the extraction section 12 may extract a document related to the first string from documents stored in the database connected to the information processing apparatus 2 via the network. The extraction section 12 stores the extracted document, in association with the first string, in the storage section 27.

The method of extracting a document related to the string carried out by the extraction section 12 is not limited. For example, the extraction section 12 may extract a document including the string. The extraction section 12 may extract a document related to the string with use of any existing search engine.

The rewriting section 13 rewrites the string. As an example, the rewriting section 13 rewrites the first string with use of the document extracted by the extraction section 12. The string rewritten by the rewriting section 13 is also referred to as the second string. The rewriting section 13 stores the second string, in association with the first string, in the storage section 27.

The method of rewriting the string carried out by the rewriting section 13 is not limited. As an example, the rewriting section 13 may generate the second string by adding a string described in the document to the first string. As another example, the rewriting section 13 may generate the second string by adding, to the first string, both a string described in the document and a string indicating an additional instruction. As another example, the rewriting section 13 may generate the second string by rewriting the first string to obtain a string indicating an additional instruction, and then by adding, to this string, a string described in the document.

The generation section 14 generates a result obtained by carrying out the language processing on the string. As an example, the generation section 14 generates a text, which is a result obtained by carrying out the language processing on the second string. As described above, the generation section 14 may use the language model M trained to generate a text based on an input text. That is, the generation section 14 may input the second string into the language model M and generate the text outputted from the language model M as a result obtained by carrying out the language processing on the second string. The result that is the text generated by the generation section 14 is also referred to as the first result. The generation section 14 stores the generated first result, in association with the second string, in the storage section 27.

The output control section 23 outputs data to the output section 26. The output control section 23 corresponds to the output section 15 in the first example embodiment described above. As an example, the output control section 23 outputs a result obtained by adding information identifying the document extracted by the extraction section 12 to the first result generated by the generation section 14. The output control section 23 may add information identifying some of multiple documents extracted by the extraction section 12, to the first result generated by the generation section 14. Examples of the information identifying the document may include the document name, the author name, and the date of publication, and the uniform resource locator (URL) that indicates where the document is stored. The result outputted by the output control section 23 is also referred to as the second result.

The output control section 23 may output, in addition to the second result, the reliability calculated by the calculation section 21 described later. With this configuration, the output control section 23 can present the reliability of the second result to the user.

The output control section 23 may be configured to output the second result as an optimized result, in a case where the determination section 22, described later, has determined that the reliability calculated by the calculation section 21 exceeds the threshold. With this configuration, the output control section 23 can output the optimized second result with high reliability.

The calculation section 21 calculates the reliability of the result. As an example, the calculation section 21 calculates the reliability of the first result (text) generated by the generation section 14. The calculation section 21 stores the calculated reliability, in association with the first result, in the storage section 27. With this configuration, the calculation section 21 can ascertain to what extent the first result is reliable.

The method of calculating the reliability of the first result carried out by the calculation section 21 is not limited. The calculation section 21 may calculate the reliability of the first result with use of existing techniques such as facticity analysis, which is a technique for analyzing whether an event has actually occurred. As an example, the calculation section 21 may calculate the reliability of the first result with use of both the first result and the document extracted by the extraction section 12. Examples of a method of calculating the reliability of the first result carried out by the calculation section 21 with use of both the first result and the document extracted by the extraction section 12 may include (a) a method based on inter-word distance, (b) a method based on inter-document distance, or (c) a method based on a learning model.

In a case where the method based on the inter-word distance is used, the calculation section 21 calculates the reliability of the first result based on the inter-word distance between a word included in the first result and a word included in the document. Specifically, the calculation section 21 first calculates the inter-word distance for each combination of a word included in the first result and a word included in the document. The calculation section 21 calculates the reliability of the first result such that the shorter the calculated inter-word distance is, the higher the reliability of the first result is.

In a case where the method based on the inter-document distance is used, the calculation section 21 calculates the reliability of the first result based on the inter-document distance between a sentence included in the first result and a sentence included in the document. Specifically, the calculation section 21 first calculates the inter-document distance between a text included in the first result and a text included in the document. The calculation section 21 calculates the reliability of the first result such that the shorter the calculated inter-document distance is, the higher the reliability of the first result is.

In a case where the method based on the learning model is used, the calculation section 21 uses a learning model that has been learned by machine learning to receive two sentences as input and to output the similarity between the two sentences. In this case, the calculation section 21 inputs, into the learning model, a sentence included in the first result and a sentence included in the document. Then, the calculation section 21 calculates the reliability of the first result such that the higher the degree of the similarity outputted from the learning model is, the higher the reliability of the first result is.

In a case where the extraction section 12 has extracted multiple documents, the calculation section 21 calculates the reliability of the first result for each of the multiple documents. The calculation section 21 may calculate an arithmetic average value of the calculated multiple reliabilities as the reliability of the first result.

As another example, the calculation section 21 may calculate the reliability with use of the first result, the document extracted by the extraction section 12, and the string acquired by the acquisition section 11. For example, the calculation section 21 may calculate the reliability, referring to a result obtained by inputting, into the language model M used by the generation section 14, the first result, the document extracted by the extraction section 12, and the string acquired by the acquisition section 11. As an example, the calculation section 21 acquires, from the language model M, an index indicating how correct the first result obtained with reference to the document is, as a response to the first string. The calculation section 21 calculates the reliability of the first result such that the higher the output result is (e.g., the larger value the index is), the higher the reliability of the first result is. With this configuration, the calculation section 21 can suitably calculate the reliability of the first result with use of the language model M that has generated the first result.

The calculation section 21 may input the first result, the document extracted by the extraction section 12, and the string acquired by the acquisition section 11 multiple times into the language model M. In this case, the calculation section 21 may score the result outputted from the language model M for each of the multiple times of input (likelihood, positive frequency, etc.), and calculate the reliability of the first result such that the higher the score is, the higher the reliability of the first result is.

Further, instead of the string acquired by the acquisition section 11, the calculation section 21 may input a string instructing to answer whether the first result is correct or not into the language model M, considering the document identified by the information added by the output control section 23. In this case also, the calculation section 21 calculates the reliability of the first result such that the more positive the output result is, the higher the reliability of the first result is.

The determination section 22 determines whether the value exceeds a threshold. As an example, the determination section 22 determines whether the reliability calculated by the calculation section 21 exceeds the threshold. The determination section 22 stores the determination result, in association with the reliability, in the storage section 27.

(Process Carried Out by Information Processing Apparatus 2)

Figure 4:
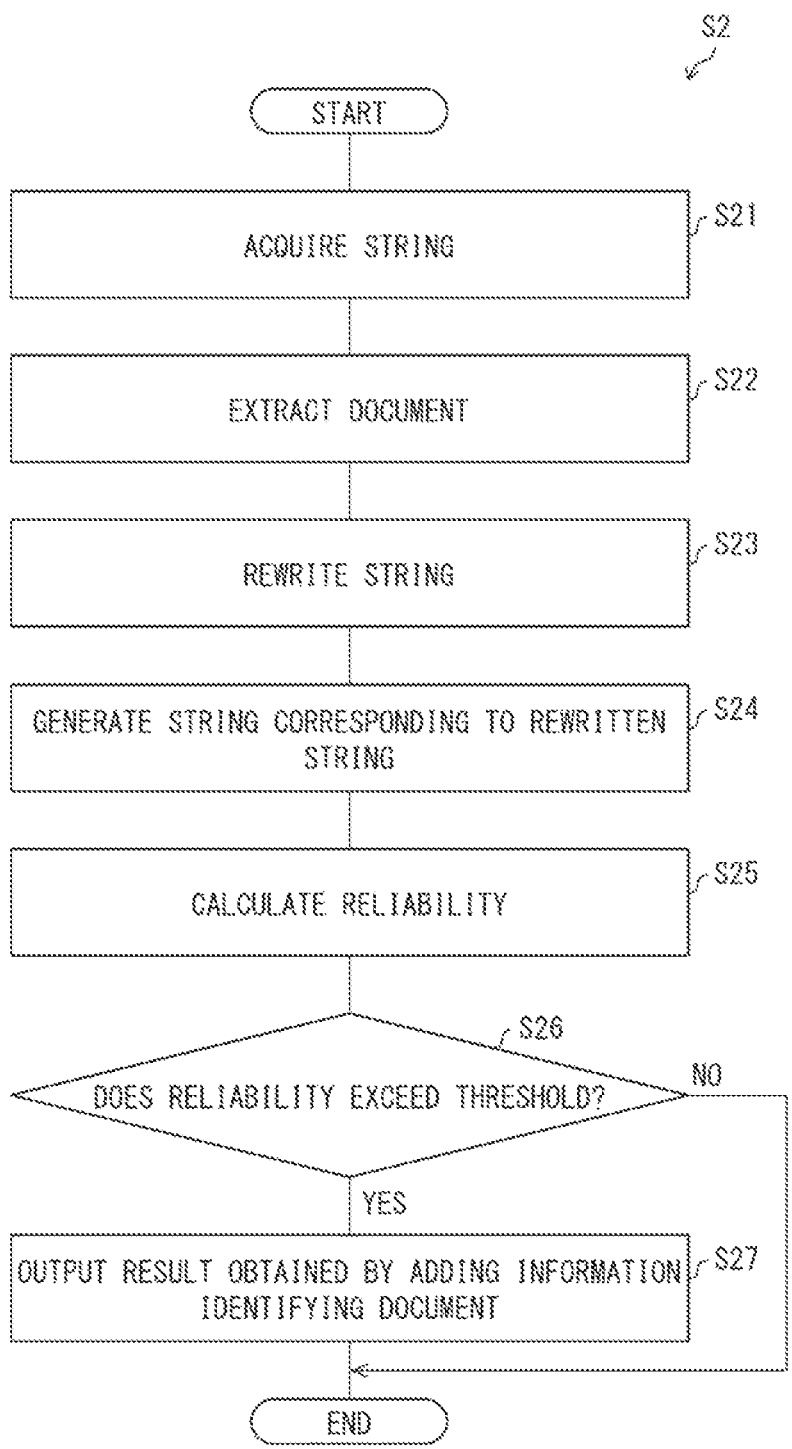
FIG. 4 is a flowchart illustrating the flow of an information processing method in accordance with the second example embodiment of the present invention.

The following description will discuss an information processing method carried out by the information processing apparatus 2, with reference to FIG. 4. FIG. 4 is a flowchart illustrating the flow of an information processing method S2 in accordance with the present example embodiment.

Figure 5:
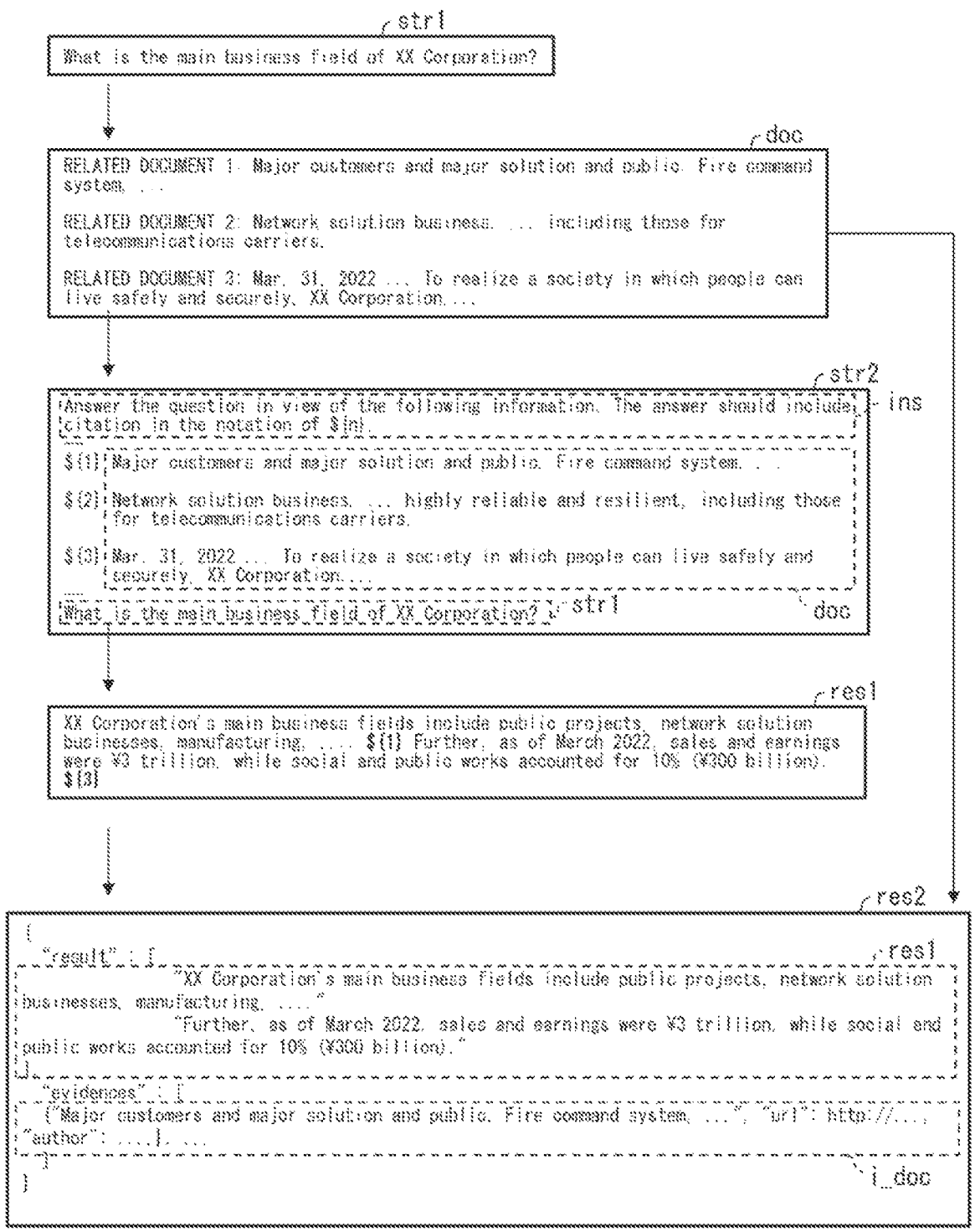
FIG. 5 is a diagram illustrating an example of each process carried out by the information processing apparatus in accordance with the second example embodiment of the present invention.

Further, an example of each process carried out by the information processing apparatus 2 will be described with reference to FIG. 5. FIG. 5 is a diagram illustrating an example of each process carried out by the information processing apparatus 2 in accordance with the present example embodiment.

(Step S21)

In step S21, the acquisition section 11 acquires a string (first string). The acquisition section 11 stores the first string in the storage section 27.

For example, as illustrated in FIG. 5, the acquisition section 11 acquires a first string str1 indicating "what is the main description of business of XX Corporation?".

(Step S22)

In step S22, the extraction section 12 extracts a document related to the first string stored in the storage section 27. The extraction section 12 stores the extracted document, in association with the first string, in the storage section 27.

For example, as illustrated in FIG. 5, the extraction section 12 extracts a document doc related to the first string str1 "what is the main description of business of XX Corporation?". The document doc includes multiple documents ("Related Document 1", "Related Document 2", "Related Document 3", etc.).

(Step S23)

In step S23, the rewriting section 13 rewrites the first string with use of the first string and the document, which are stored in the storage section 27, to generate a second string. The rewriting section 13 stores the second string, in association with the first string, in the storage section 27.

For example, as illustrated in FIG. 5, the rewriting section 13 generates the second string str2 by adding the document doc to the first string str1.

The rewriting section 13 may generate the second string str2 by adding an instruction. For example, the rewriting section 13 may generate the second string str2 by adding a string that instructs to add the document referred to generate the first result, to a section obtained with reference to the document. As an example, as illustrated in FIG. 5, the rewriting section 13 may add, to the second string str2, a string ins that indicates an additional instruction, that is, "Answer the question in view of the following information. The answer should include citation in the notation of ${n}." This instruction instructs the language model M, when the result of the language model M includes a string that is obtained with reference to a document "${n}", to add the document "${n}" to the string.

(Step S24)

In step S24, the generation section 14 generates a string (first result) corresponding to the second string stored in the storage section 27 with use of the language model M trained to generate a text based on the input text. The generation section 14 stores the first result, in association with the second string, in the storage section 27.

For example, as illustrated in FIG. 5, the generation section 14 inputs the second string str2 into the language model M, to generate a first result res1 outputted from the language model M.

(Step S25)

In step S25, the calculation section 21 calculates the reliability of the first result stored in the storage section 27. The calculation section 21 stores the calculated reliability, in association with the first result, in the storage section 27.

For example, as illustrated in FIG. 5, the calculation section 21 calculates the reliability with use of the first result res1, the document doc, and the first string str1. As an example, the calculation section 21 inputs the first result res1, the document doc, and the first string str1 into the language model M. In this case, the calculation section 21 acquires, from the language model M, an index indicating how correct the first result res1 obtained with reference to the document doc is, as a response to the first string str1. The calculation section 21 calculates the reliability with reference to the index.

Further, as an example, instead of the document doc, the calculation section 21 may input a document (${1} or ${3}) included in the first result res1 illustrated in FIG. 5 into the language model M, to calculate the reliability. Further, for example, instead of the first string str1, the calculation section 21 may input, into the language model M, the string "can it be said that the first result res1 is correct when considering the information of the document indicated by ${1}?", to calculate the reliability.

(Step S26)

In step S26, the determination section 22 determines whether the reliability stored in the storage section 27 exceeds the threshold.

(Step S27)

In a case where it has been determined that the reliability exceeds the threshold in step S26 (step S26: YES), then, in step S27, the output control section 23 generates a result (second result) obtained by adding information identifying the document stored in the storage section 27 to the first result stored in the storage section 27. The output control section 23 outputs the generated second result as an optimized result.

For example, as illustrated in FIG. 5, the output control section 23 generates a second result res2 obtained by adding information i_doc identifying the document to the first result res1.

The output control section 23 may be configured to add information identifying only a document that has been referred to when the language model M generates the first result res1, among the documents doc extracted by the extraction section 12. This configuration can be realized by adding, to the second string str2, the string ins indicating the abovementioned additional instruction, that is, "Answer the question in view of the following information. The answer should include citation in the notation of ${n}."

For example, it is assumed that the first result res1 includes "${1}" and "${3}" as illustrated in FIG. 5. In this case, the output control section 23 adds the information i_doc identifying the document indicated by "${1}" and the document indicated by "${3}" to the first result res1, to generate the second result res2.

On the other hand, in a case where it has been determined that the reliability does not exceed the threshold in step S26 (step S26: NO), the information processing apparatus 2 terminates the information processing method S2 without causing the output control section 23 to output the second result.

(Example Advantage of Information Processing Apparatus 2)

Thus, the information processing apparatus 2 in accordance with the present example embodiment carries out language processing, with use of the language model M, on the second string obtained by rewriting the first string with use of the acquired document related to the first string. Therefore, the information processing apparatus 2 can prevent the language model M from carrying out the language processing with reference to a document in which correctness of the contents is unknown, such as a less reliable document, a document that is unclear whether the contents are true or false, and a document whose origin is unknown. Therefore, the information processing apparatus 2 can improve the reliability of the result of the language processing carried out with use of the language model M.

Further, the information processing apparatus 2 outputs a result obtained by adding the information identifying the document related to the first string to the result obtained by the language model M carrying out the language processing on the second string. Therefore, the information processing apparatus 2 can present the user with both the result obtained by carrying out the language processing and the information on the document referred to in the language processing. Therefore, the information processing apparatus 2 can present the user with the reliability of the language processing carried out with use of the language model.

Third Example Embodiment

The following description will discuss a third example embodiment of the present invention in detail with reference to the drawings. The same reference numerals are given to constituent elements which have functions identical to those described in the above example embodiments, and descriptions as to such constituent elements are omitted as appropriate.

(Outline and Configuration of Information Processing System 100)

Figure 6:
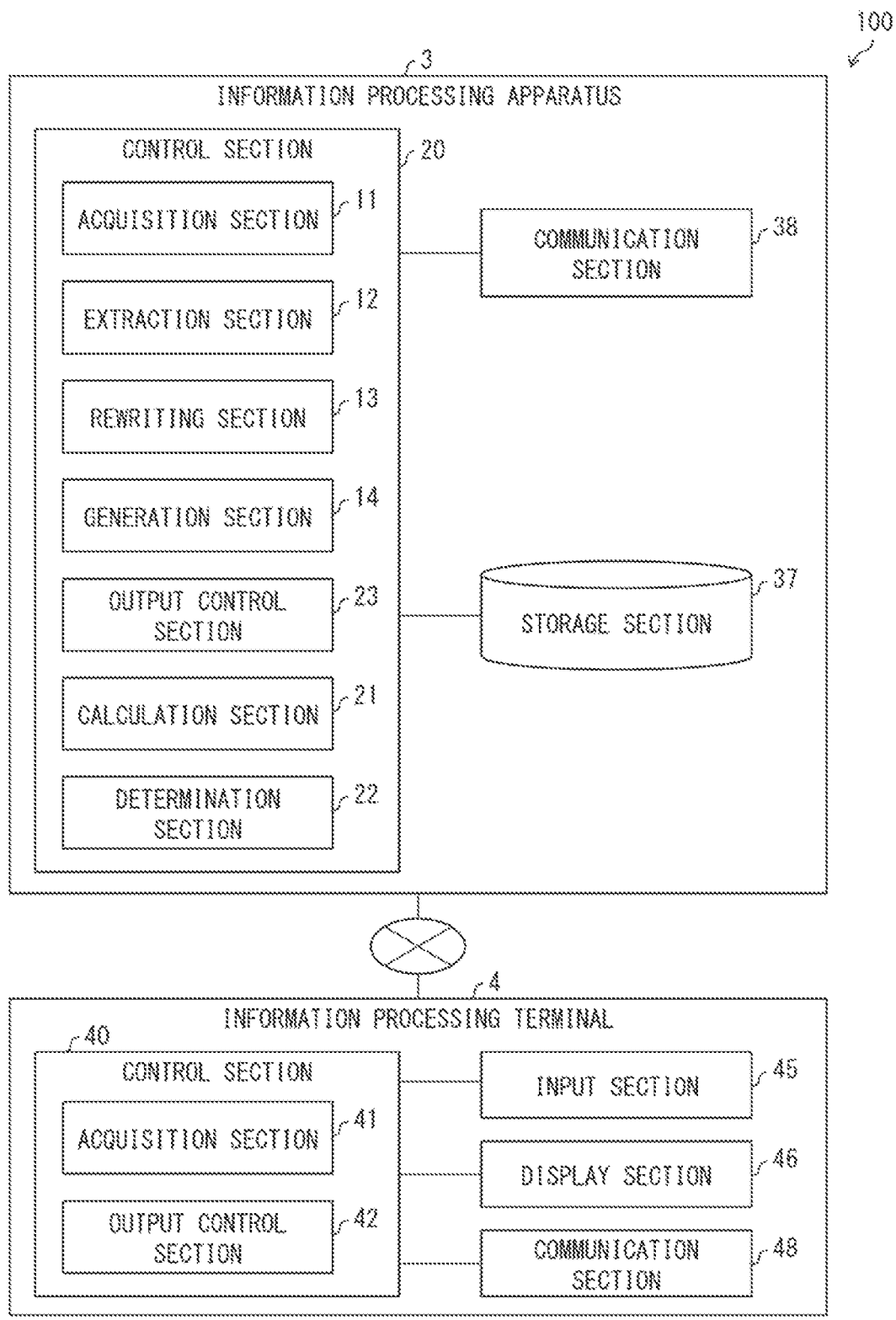
FIG. 6 is a block diagram illustrating the configuration of an information processing system in accordance with a third example embodiment of the present invention.

The following description will discuss the outline and the configuration of an information processing system 100 in accordance with the present example embodiment with reference to FIG. 6. FIG. 6 is a block diagram illustrating the configuration of the information processing system 100 in accordance with the present example embodiment.

As illustrated in FIG. 6, the information processing system 100 includes an information processing apparatus 3 and an information processing terminal 4. The information processing apparatus 3 and the information processing terminal 4 are connected via a network so that they can communicate with each other. An example of the information processing apparatus 3 may be a stationary computer. Examples of the information processing terminal 4 may include a smartphone, a tablet terminal, and a laptop computer.

In the information processing system 100, the information processing terminal 4 acquires a target text, and the information processing apparatus 3 carries out language processing on the target text with use of a language model M. Further, the information processing apparatus 3 outputs a result obtained by carrying out the language processing to the information processing terminal 4. Also in the following description, the "target text" and the "text" are also referred to as the "string".

As an example, in the information processing system 100, the user of the information processing terminal 4 creates an account for using the information processing system 100 and registers the basic information (name, age, gender, email address, etc.). When the user inputs a string related to medical counseling into the information processing terminal 4, the information processing apparatus 3 outputs a response to the medical counseling. Examples of the user input may include symptoms, chronic diseases, and usage conditions of drugs. In response to the medical counseling, the information processing apparatus 3 outputs, in addition to the response, information that supports the response.

(Configuration of Information Processing Apparatus 3)

As illustrated in FIG. 6, the information processing apparatus 3 includes a control section 20, a storage section 37, and a communication section 38.

The storage section 37 is identical in configuration and function to the storage section 27 described above. Further, the storage section 37 stores documents and information on authors of the documents.

FIGS. 7 and 8 show examples of the documents and the information on authors stored in the storage section 37. FIG. 7 is a table showing an example of the documents in the present example embodiment. FIG. 8 is a table showing an example of the information on the authors of the documents in the present example embodiment.

As illustrated in FIG. 7, the documents stored in the storage section 37 is those regarding healthcare. As illustrated in FIG. 7, each document stored in the storage section 37 may be stored in such a manner as to be associated with the author or authors, the year of publication, and the summary of the paper.

Further, as illustrated in FIG. 8, information on each author who wrote a document stored in the storage section 37 may be stored in the storage section 37. As illustrated in FIG. 8, as the information on an author who wrote a document, the name of the doctor, the workplace, the career, and the specialty may be stored in the storage section 37.

Thus, the document in the information processing system 100 is a document regarding healthcare and is a document in which the career, specialty, or the like of the author of the document is clear. Therefore, it can be said that the document regarding healthcare in the information processing system 100 is a highly reliable document.

The communication section 38 is an interface for transmitting and receiving data to and from an external apparatus via a network. As an example, the communication section 38 transmits data provided by the control section 20 to the information processing terminal 4 and provides data received from the information processing terminal 4 to the control section 20. Examples of the communication section 38 may include, but not limited to, a communication chip in various communication standards such as Ethernet (registered trademark), Wi-Fi (registered trademark), and radio communications standard for mobile data communications networks, and a USB-compliant connector.

The control section 20 controls constituent elements included in the information processing apparatus 3. Further, as illustrated in FIG. 6, the control section 20 includes an acquisition section 11, an extraction section 12, a rewriting section 13, a generation section 14, an output control section 23, a calculation section 21, and a determination section 22. The acquisition section 11, the extraction section 12, the rewriting section 13, the generation section 14, the output control section 23, the calculation section 21, and the determination section 22 are configured to realize acquisition means, extraction means, rewriting means, generation means, output means, calculation means, and determination means, respectively, in the present example embodiment.

The acquisition section 11 acquires data provided by the communication section 38. As an example, the acquisition section 11 acquires a first string. The acquisition section 11 stores the acquired first string in the storage section 37.

The extraction section 12 extracts a document related to the string. The method of extracting the document carried out by the extraction section 12 is as described above. Further, the extraction section 12 acquires, from the storage section 37, information on an author of the extracted document. The extraction section 12 stores the extracted document and the information on the author of the extracted document in the storage section 37, in association with the first string.

The rewriting section 13 rewrites the string. The method of rewriting the first string and generating the second string, carried out by the rewriting section 13, is as described above.

The generation section 14 generates a result obtained by carrying out the language processing on the string. As described above, the generation section 14 generates a first result obtained by carrying out the language processing on the second string. The method of generating the first result carried out by the generation section 14 is as described above. The generation section 14 stores the generated first result, in association with the second string, in the storage section 37.

The output control section 23 outputs data to the communication section 38. As an example, the output control section 23 outputs a result obtained by adding information identifying the document extracted by the extraction section 12 to the first result generated by the generation section 14. Further, the output control section 23 may output a result obtained by adding the information on the author of the document extracted by the extraction section 12.

Further, as described above, the output control section 23 may output, in addition to the second result, the reliability calculated by the calculation section 21.

The output control section 23 may be configured to output the second result in a case where the determination section 22 has determined that the reliability calculated by the calculation section 21 exceeds the threshold.

The calculation section 21 calculates the reliability of the result. As an example, the calculation section 21 calculates the reliability of the first result generated by the generation section 14. The method of calculating the reliability of the first result carried out by the calculation section 21 is as described above. The calculation section 21 stores the calculated reliability, in association with the first result, in the storage section 37.

The determination section 22 determines whether the value exceeds a threshold. As an example, the determination section 22 determines whether the reliability calculated by the calculation section 21 exceeds the threshold. The determination section 22 stores the determination result, in association with the reliability, in the storage section 37.

(Configuration of Information Processing Terminal 4)

As illustrated in FIG. 6, the information processing terminal 4 includes a control section 40, an input section 45, a display section 46, and a communication section 48.

The control section 40 controls constituent elements included in the information processing terminal 4. Further, as illustrated in FIG. 6, the control section 40 includes an acquisition section 41 and an output control section 42.

The acquisition section 41 acquires data provided by the input section 45 or the communication section 48. As an example, the acquisition section 41 acquires a string from the input section 45. As another example, the acquisition section 41 acquires a second result from the communication section 48. The acquisition section 41 provides the acquired data to the output control section 42.

The output control section 42 outputs the data to the display section 46 or the communication section 48. As an example, the output control section 42 outputs the string acquired by the acquisition section 41 to the communication section 48. As another example, the output control section 42 outputs the second result acquired by the acquisition section 41 to the display section 46.

The input section 45 is an interface for receiving data input. Examples of the input section 45 may include a mouse, a keyboard, a touch pad, and a microphone. The input section 45 provides the received data to the control section 40.

The display section 46 is a device for displaying an image. As an example, the display section 46 displays an image based on the data provided by the control section 40. Examples of the display section 46 may include a liquid crystal display and an organic electro luminescence (EL) display.

The communication section 48 is an interface for transmitting and receiving data to and from an external apparatus via a network. As an example, the communication section 48 transmits the data provided by the control section 40 to the information processing apparatus 3 and provides data received from the information processing apparatus 3 to the control section 40. Examples of the communication section 48 may include, but not limited to, a communication chip in various communication standards such as Ethernet, Wi-Fi, and radio communications standard for mobile data communications networks, and a USB-compliant connector.

(Process Carried Out in Information Processing System 100)

The following description will discuss an information processing method carried out in the information processing system 100, with reference to FIG. 9. FIG. 9 is a flowchart illustrating the flow of an information processing method S100 in accordance with the present example embodiment.

(Step S101)

In step S101, the acquisition section 41 of the information processing terminal 4 acquires a string (first string). The acquisition section 41 provides the first string to the output control section 42.

(Step S102)

In step S102, the output control section 42 outputs the first string provided by the acquisition section 41 to the information processing apparatus 3 via the communication section 48.

(Step S103)

In step S103, the acquisition section 11 of the information processing apparatus 3 acquires, via the communication section 38, the first string outputted from the information processing terminal 4. The acquisition section 11 stores the first string in the storage section 37.

(Step S104)

In step S104, the extraction section 12 extracts a document related to the first string stored in the storage section 37. Further, the extraction section 12 acquires, from the storage section 37, information on an author of the extracted document. The extraction section 12 stores the extracted document and the information on the author of the document in the storage section 37, in association with the first string.

(Step S105)

In step S105, the rewriting section 13 rewrites the first string with use of the first string and the document, which are stored in the storage section 37, to generate a second string. The rewriting section 13 stores the second string, in association with the first string, in the storage section 37.

(Step S106)

In step S106, the generation section 14 generates a string (first result) corresponding to the second string stored in the storage section 37 with use of the language model M trained to generate a text based on the input text. The generation section 14 stores the first result, in association with the second string, in the storage section 37.

(Step S107)

In step S107, the calculation section 21 calculates the reliability of the first result stored in the storage section 37. The calculation section 21 stores the calculated reliability, in association with the first result, in the storage section 37.

(Step S108)

In step S108, the determination section 22 determines whether the reliability stored in the storage section 37 exceeds the threshold.

(Step S109)

In a case where it has been determined that the reliability exceeds the threshold in step S108 (step S108: YES), then, in step S109, the output control section 23 generates a result (second result) obtained by adding information identifying the document stored in the storage section 37 to the first result stored in the storage section 37, as an optimized result. The output control section 23 may add, to the second result, the result obtained by adding the information on the author of the document stored in the storage section 37. The output control section 23 outputs, via the communication section 38, the generated second result to the information processing terminal 4.

(Step S110)

In step S110, the acquisition section 41 of the information processing terminal 4 acquires, via the communication section 48, the second result outputted from the information processing apparatus 3. The acquisition section 41 provides the acquired second result to the output control section 42.

(Step S111)

In step S111, the output control section 42 displays the second result provided by the acquisition section 41 on the display section 46.

On the other hand, in a case where it has been determined that the reliability does not exceed the threshold in step S108 (step S108: NO), the information processing system 100 terminates the information processing method S100 without causing the output control section 23 to output the second result.

Alternatively, the output control section 23 may output, to the information processing terminal 4, information indicating that no highly reliable result could be generated, via the communication section 38. In this case, the output control section 42 of the information processing terminal 4 may display on the display section 46 that no reliable result could be generated.

(First Example of Image Displayed by Information Processing Terminal 4)

An example of the image displayed by the information processing terminal 4 will be described with reference to FIG. 10. FIG. 10 is a diagram illustrating an example of images displayed on the information processing terminal 4 in accordance with the present example embodiment.

As described above, the output control section 42 of the information processing terminal 4 displays the second result on the display section 46. As an example, as illustrated at the left diagram of FIG. 10, the output control section 42 displays the second result res, that is, "Have you also noticed either eye sensitivity to light or slurring of your speech?", in response to the input, "Moderate", which indicates a symptom and is inputted by the user.

As an example, the output control section 42 may display information identifying the document in addition to the second result res. As another example, when the acquisition section 41 acquires information indicating an operation indicating that the user selects the second result res (e.g., an operation performed by touching a portion in the display section 46 at which the second result res is displayed), the output control section 42 may display information identifying the document. Further, as described above, a case where the output control section 23 of the information processing apparatus 3 outputs the second result obtained by adding information on the author of the document, the output control section 42 may display information on the author of the document in addition to the information identifying the document.

Second Example of Image Displayed by Information Processing Terminal 4

In step S109 described above, the output control section 23 may output, in addition to the second result, information for communicating with a doctor, to the information processing terminal 4. As an example, the output control section 23 may refer to the information identifying the document and the information on the author of the document, and then may output the contact information of a doctor in the same professional field as that of the author to the information processing terminal 4, in addition to the second result.

For example, when the output control section 23 outputs the doctor's contact information to the information processing terminal 4 in addition to the second result in the abovementioned step S109, the information processing terminal 4 displays the doctor's contact information on the display section 46 in addition to the second result. In this configuration, when the acquisition section 41 acquires information indicating an operation indicating that the user selects the doctor's contact information (e.g., an operation performed by touching a portion in the display section 46 at which the doctor's contact information is displayed), the output control section 42 establishes contact with the doctor using the contact information.

With this configuration, the information processing terminal 4 enables the user to make a video call with the doctor as illustrated in the central diagram in FIG. 10.

Third Example of Image Displayed by Information Processing Terminal 4

In step S109 described above, the output control section 23 may output, to the information processing terminal 4, information on an action proposed to the user, in addition to the second result. Examples of actions proposed to the user may include going to a hospital and obtaining a doctor's prescription medicine. The following description will discuss a configuration in which the output control section 23 outputs, to the information processing terminal 4, information indicating a method of obtaining a doctor's prescription medicine.

In a case where the second result includes information identifying a medicine, the output control section 23 may output, to the information processing terminal 4, the place of a pharmacy where the medicine is sold, in addition to the second result.

Alternatively, as described above, after the user communicates with the doctor, the doctor may output a prescription for the user to the information processing terminal 4. When the user obtains the prescription, the information processing terminal 4 may output, in addition to the second result, to the information processing terminal 4, the place of a pharmacy where the medicine is sold, described in the prescription.

With this configuration, as illustrated in the right diagram in FIG. 10, the information processing terminal 4 can present the user with a place where the user can purchase the medicine prescribed by the doctor.

First Example Advantage of Information Processing System 100

Thus, in the information processing system 100 in accordance with the present example embodiment, the information processing apparatus 3 carries out language processing on the second string obtained by rewriting the first string with use of the document related to the first string acquired from the information processing terminal 4, with use of the language model M. Therefore, the information processing apparatus 3 can prevent the language model M from carrying out the language processing with reference to a document in which correctness of the contents is unknown, such as a less reliable document, a document that is unclear whether the contents are true or false, and a document whose origin is unknown. Therefore, the information processing apparatus 3 can improve the reliability of the result of the language processing carried out with use of the language model M.

Further, in the information processing system 100 in accordance with the present example embodiment, the information processing apparatus 3 outputs the result obtained by adding the information identifying the document related to the first string to the result obtained by the language model M carrying out language processing on the second string. Therefore, the information processing apparatus 3 can present the user with both the result obtained by carrying out the language processing and the information on the document referred to in the language processing. Therefore, the information processing apparatus 3 can present the user with the reliability of the language processing carried out with use of the language model.

Second Example Advantage of Information Processing System 100

In the information processing system 100, the information processing terminal 4 take a question in medical counseling, and the information processing apparatus 3 generates a response to the medical counseling. The following description will discuss an example advantage achieved in a configuration in which the information processing system 100 outputs a response to medical counseling of the user.

First, in the information processing system 100, the information processing apparatus 3 generates a response to the medical counseling with use of the language model M. In the configuration, the user takes medical counseling via the information processing terminal 4 such as, for example, a smartphone. Therefore, with the information processing system 100, the user can easily take medical counseling. Further, with the information processing system 100, the user can easily take medical counseling anytime and anywhere. Further, with the information processing system 100, for example, the user can receive general information and/or advice about symptoms at a stage before the user receives any diagnosis or treatment.

Further, since the information processing terminal 4 allows the user to ask medical counseling therethrough and outputs a response, the user can take medical counseling without going to the hospital. Further, the information processing system 100 allows the user to obtain a response to medical counseling more quickly than when the user go to the hospital. Further, in the information processing system 100, response to the medical counseling can be provided without intervention by a doctor, resulting in a decrease in cost of responding to medical counseling.

Further, the language model M used by the information processing apparatus 3 carries out language processing with reference to documents. For example, the information processing apparatus 3 causes the language model M to carried out language processing with reference to documents written by medical specialists, not to documents in which the reliabilities are suspected, such as news articles on the internet. Therefore, the information processing apparatus 3 can present information with higher reliability compared to the case where the conventional language model is used.

Software Implementation Example

Some or all of the functions of the information processing apparatuses 1, 2, and 3 may be realized by hardware such as an integrated circuit (IC chip) or may be alternatively realized by software.

Figure 11:
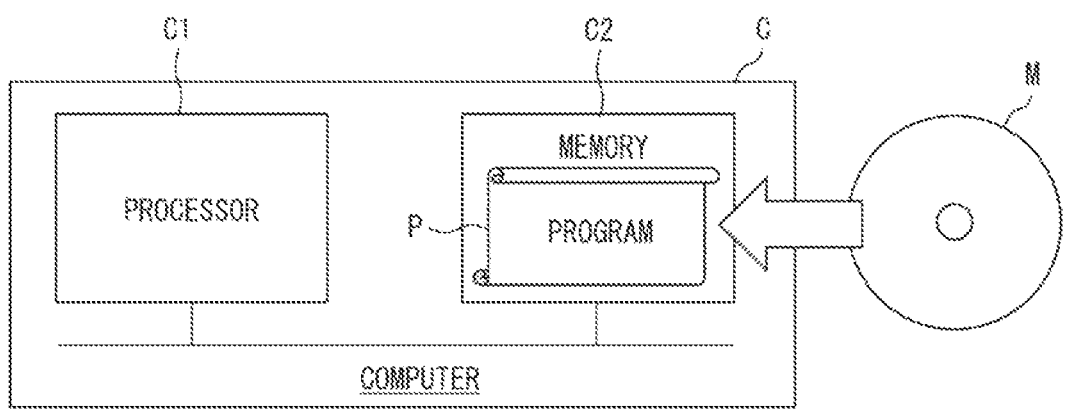
FIG. 11 is a block diagram illustrating an example of the hardware configuration of the information processing apparatus in accordance with each of the example embodiments of the present invention.

In the latter case, the information processing apparatuses 1, 2, and 3 are each realized by, for example, a computer that executes instructions of a program that is software realizing the functions. FIG. 11 illustrates an example of such a computer (hereinafter referred to as "computer C"). The computer C includes at least one processor C1 and at least one memory C2. The memory C2 stores a program P for causing the computer C to operate as each of the information processing apparatuses 1, 2, and 3. In the computer C, the functions of each of the information processing apparatuses 1, 2, and 3 are realized by the processor C1 reading the program P from the memory C2 and executing the program P.

The processor C1 may be, for example, a central processing unit (CPU), a graphic processing unit (GPU), a digital signal processor (DSP), a micro processing unit (MPU), a floating point number processing unit (FPU), a physics processing unit (PPU), a tensor processing unit (TPU), a quantum processor, a microcontroller, or a combination thereof. The memory C2 may be, for example, a flash memory, a hard disk drive (HDD), a solid state drive (SSD), or a combination thereof.

Note that the computer C may further include a random access memory (RAM) in which the program P is loaded when the program P is executed and/or in which various kinds of data are temporarily stored. The computer C may further include a communication interface for transmitting and receiving data to and from another apparatus. The computer C may further include an input/output interface for connecting the computer C to an input/output apparatus(es) such as a keyboard, a mouse, a display and/or a printer.

The program P can be recorded in a non-transitory tangible storage medium M from which the computer C can read the program P. Such a storage medium M may be, for example, a tape, a disk, a card, a semiconductor memory, a programmable logic circuit, or the like. The computer C can acquire the program P via the storage medium M. The program P can be transmitted via a transmission medium. The transmission medium may be, for example, a communications network, a broadcast wave, or the like. The computer C can acquire the program P also via such a transmission medium.

Additional Remark 1

The present invention is not limited to the foregoing example embodiments, but may be altered in various ways by a skilled person within the scope of the claims. For example, the present invention also encompasses, in its technical scope, any example embodiment derived by appropriately combining technical means disclosed in the foregoing example embodiments.

Additional Remark 2

Some or all of the above example embodiments can be described as below. However, the present invention is not limited to example aspects described below.

Supplementary Note 1

A language processing apparatus including: acquisition means for acquiring a target text; extraction means for extracting a document related to the target text; rewriting means for rewriting the target text with use of the document; generation means for generating a text corresponding to the rewritten target text with use of a language model trained to generate a text based on an input text; and output means for outputting a result obtained by adding information identifying the document to the text generated by the generation means.

Supplementary Note 2

The information processing apparatus according to Supplementary note 1, further including calculation means for calculating reliability of the text generated by the generation means.

Supplementary Note 3

The information processing apparatus according to Supplementary note 2, further including determination means for determining whether the reliability exceeds a threshold, wherein, in a case where the determination means has determined that the reliability exceeds the threshold, the output means outputs the result obtained by adding the information identifying the document as an optimized result.

Supplementary Note 4

The information processing apparatus according to Supplementary note 2 or 3, wherein the output means outputs the reliability in addition to the result obtained by adding the information identifying the document.

Supplementary Note 5

The information processing apparatus according to Supplementary note 4, wherein the calculation means calculates the reliability, referring to a result obtained by inputting, to the language model, the text generated by the generation means, the document extracted by the extraction means, and the target text acquired by the acquisition means.

Supplementary Note 6

An information processing method including: acquiring, by at least one processor, a target text; extracting, by the at least one processor, a document related to the target text; rewriting, by the at least one processor, the target text with use of the document; generating, by the at least one processor, a text corresponding to the rewritten target text with use of a language model trained to generate a text based on an input text; and outputting, by the at least one processor, a result obtained by adding information identifying the document to the text generated in the generating.

Supplementary Note 7

A program for causing a computer to carry out: an acquisition process of acquiring a target text; an extraction process of extracting a document related to the target text; a rewriting process of rewriting the target text with use of the document; a generation process of generating a text corresponding to the rewritten target text with use of a language model trained to generate a text based on an input text; and an output process of outputting a result obtained by adding information identifying the document to the text generated in the generation process.

Additional Remark 3

Some or all of the above example embodiments can also be described as below.

Supplementary Note 1

An information processing apparatus including at least one processor, the at least one processor carrying out: an acquisition process of acquiring a target text; an extraction process of extracting a document related to the target text; a rewriting process of rewriting the target text with use of the document; a generation process of generating a text corresponding to the rewritten target text with use of a language model trained to generate a text based on an input text; and an output process of outputting a result obtained by adding information identifying the document to the text generated in the generation process.

Supplementary Note 2

The information processing apparatus according to Supplementary note 1, wherein the at least one processor further carrying out a calculation process of calculating reliability of the text generated in the generation process.

Supplementary Note 3

The information processing apparatus according to Supplementary note 2, wherein the at least one processor further carrying out a determination process of determining whether the reliability exceeds a threshold, wherein in a case where it has been determined, in the determination process, that the reliability exceeds the threshold, the result obtained by adding the information identifying the document is outputted as an optimized result in the output process.

Supplementary Note 4

The information processing apparatus according to Supplementary note 2 or 3, wherein, in the output process, the reliability is outputted in addition to the result obtained by adding the information identifying the document.

Supplementary Note 5

The information processing apparatus according to Supplementary note 4, wherein, in the calculation process, the reliability is calculated by referring to a result obtained by inputting, to the language model, the text generated in the generation process, the document extracted in the extraction process, and the target text acquired in the acquisition process.

Note that the information processing apparatus may further include a memory, and this memory may include a program for causing the processor to carry out the acquisition process, the extraction process, the rewriting process, the generation process, the output process, the calculation process, and the determination process. The program may be stored in a computer-readable, non-transitory, tangible storage medium.

REFERENCE SIGNS LIST 1, 2, 3 Information processing apparatus
11 Acquisition section
12 Extraction section
13 Rewriting section
14 Generation section
15 Output section
21 Calculation section
22 Determination section
23 Output control section
C1 Processor
C2 Memory
doc Document
res, res2 Second result
res1 First result
str1 First string
str2 Second string

What is claimed is:
1. An information processing apparatus comprising:
a memory storing instructions; and
at least one processor configured to execute the instructions to perform processes comprising:
an acquisition process of acquiring a target text;
an extraction process of extracting a document related to the target text;
a rewriting process of rewriting the target text with use of the document;
a generation process of generating a text corresponding to the rewritten target text with use of a machine learning model trained to generate a text based on an input text;
a calculation process of calculating reliability of the text generated in the generation process; and
an output process of outputting a result obtained by adding information identifying the document to the text generated in the generation process, and of outputting the reliability of the text generated in the generation process,
wherein the calculation process includes referring to a result obtained by inputting, to the machine learning model, the text generated in the generation process, the document extracted in the extraction process, and the target text acquired in the acquisition process.
2. The information processing apparatus according to claim 1, wherein
the processes further comprise a determination process of determining whether the reliability exceeds a threshold,
in a case where the reliability has been determined to exceed the threshold, the output process includes outputting the result obtained by adding the information identifying the document as an optimized result.
3. An information processing method performed by at least one processor and comprising:
an acquisition process of acquiring a target text;
an extraction process of extracting a document related to the target text;
a rewriting process of rewriting the target text with use of the document;
a generation process of generating a text corresponding to the rewritten target text with use of a machine learning model trained to generate a text based on an input text;
a calculation process of calculating reliability of the text generated in the generation process; and
an output process of outputting a result obtained by adding information identifying the document to the text generated in the generation process, and of outputting the reliability of the text generated in the generation process,
wherein the calculation process includes referring to a result obtained by inputting, to the machine learning model, the text generated in the generation process, the document extracted in the extraction process, and the target text acquired in the acquisition process.
4. A non-transitory storage medium storing a program executable by a computer to perform processes comprising:
an acquisition process of acquiring a target text;
an extraction process of extracting a document related to the target text;
a rewriting process of rewriting the target text with use of the document;
a generation process of generating a text corresponding to the rewritten target text with use of a machine learning model trained to generate a text based on an input text;
a calculation process of calculating reliability of the text generated in the generation process; and an output process of outputting a result obtained by adding information identifying the document to the text generated in the generation process, and of outputting the reliability of the text generated in the generation process, wherein the calculation process includes referring to a result obtained by inputting, to the machine learning model, the text generated in the generation process, the document extracted in the extraction process, and the target text acquired in the acquisition process.

* * * * *

UNITED STATES PATENT AND TRADEMARK OFFICE
CERTIFICATE OF CORRECTION

| | | |
|---|---|---|
| PATENT NO. | : 12,405,981 B2 | Page 1 of 1 |
| APPLICATION NO. | : 18/554311 | |
| DATED | : September 2, 2025 | |
| INVENTOR(S) | : Masafumi Oyamada | |

It is certified that error appears in the above-identified patent and that said Letters Patent is hereby corrected as shown below:

On the Title Page

Item (54) and in the Specification Column 1, Lines 1-3 please replace the title with the following: INFORMATION PROCESSING APPARATUS, INFORMATION PROCESSING METHOD, AND STORAGE MEDIUM FOR DECISION MAKING SUPPORT Signed and Sealed this
Thirteenth Day of January, 2026

John A. Squires
*Director of the United States Patent and Trademark Office*